United States Patent [19]

Bilstad et al.

[11] 4,314,143
[45] Feb. 2, 1982

[54] BLOOD WARMING APPARATUS WITH DIGITAL DISPLAY AND MONITORING CIRCUIT

[75] Inventors: Arnold C. Bilstad, Deerfield; John T. Foley, Wheeling, both of Ill.

[73] Assignee: Baxter Travenol Laboratories, Inc., Deerfield, Ill.

[21] Appl. No.: 53,547

[22] Filed: Jun. 29, 1979

[51] Int. Cl.³ .............................................. H05B 1/02
[52] U.S. Cl. ..................... 219/497; 219/506; 219/505; 73/362 AR; 128/214 B
[58] Field of Search ............... 219/497, 295, 499, 441, 219/506, 442, 492, 505, 327, 328; 73/362 AR; 324/62, 65; 340/347 AD, 347 M; 128/214 A, 214 B

[56] References Cited

U.S. PATENT DOCUMENTS

| | | | |
|---|---|---|---|
| 3,175,075 | 3/1965 | Nord et al. | 219/302 X |
| 3,475,590 | 10/1969 | Pins | 128/214 A |
| 3,531,990 | 10/1970 | Shinskey | 73/342 |
| 3,541,436 | 11/1970 | Haggan | 324/62 |
| 3,729,998 | 5/1973 | Mueller et al. | 73/362 AR |
| 3,817,104 | 6/1974 | Sapir | 73/362 AR |
| 3,851,528 | 12/1974 | Nichols et al. | 73/362 AR |
| 3,860,715 | 11/1977 | Scott | 364/557 |
| 3,876,933 | 4/1975 | Herrington | 324/62 |
| 3,893,192 | 7/1975 | Jensen | 324/65 R |
| 4,000,454 | 12/1976 | Brakl | 73/362 AR |
| 4,025,847 | 5/1977 | Washburn | 73/362 AR |
| 4,030,363 | 6/1977 | Halleck | 340/347 AD |
| 4,071,823 | 1/1978 | Okayama | 324/123 R |
| 4,072,051 | 2/1978 | Peterson | 73/362 AR |
| 4,096,748 | 6/1978 | Pichon | 73/362 AR |
| 4,106,341 | 8/1978 | Serrano | 73/362 AR |
| 4,107,667 | 8/1978 | Kronlage | 73/362 AR |
| 4,122,722 | 10/1978 | Newell | 73/362 AR |
| 4,161,880 | 7/1979 | Prosky | 73/362 AR |
| 4,167,663 | 9/1979 | Granzow et al. | 219/497 |
| 4,176,556 | 12/1979 | Takenaka | 73/362 AR |

Primary Examiner—Gene Z. Rubinson
Assistant Examiner—Mark H. Paschall
Attorney, Agent, or Firm—Paul Flattery; Eugene Cummings

[57] ABSTRACT

An apparatus for warming blood and other parenteral fluids as they are infused through a disposable flow system includes a pair of heating elements which heat the blood as it passes through a warming bag provided in the flow system. The heating elements are recurringly switched on and off with a duty cycle dependent on both the temperature of the blood at the output of the warming bag and the temperature differential between the output and input of the bag to maintain the blood at a predetermined temperature independent of flow rate. A digital display and monitoring circuit provides a highly accurate digital indication of blood temperature and interrupts the application of power to the heating elements in the event the temperature exceeds a predetermined maximum level.

8 Claims, 11 Drawing Figures

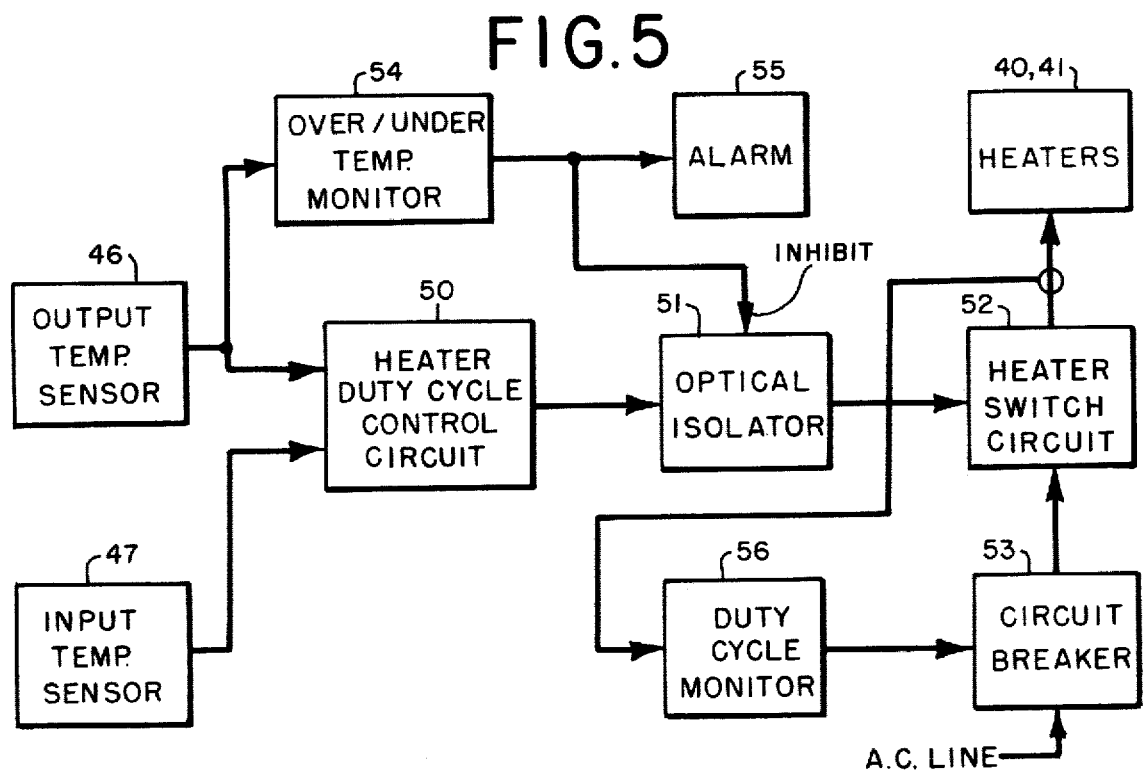
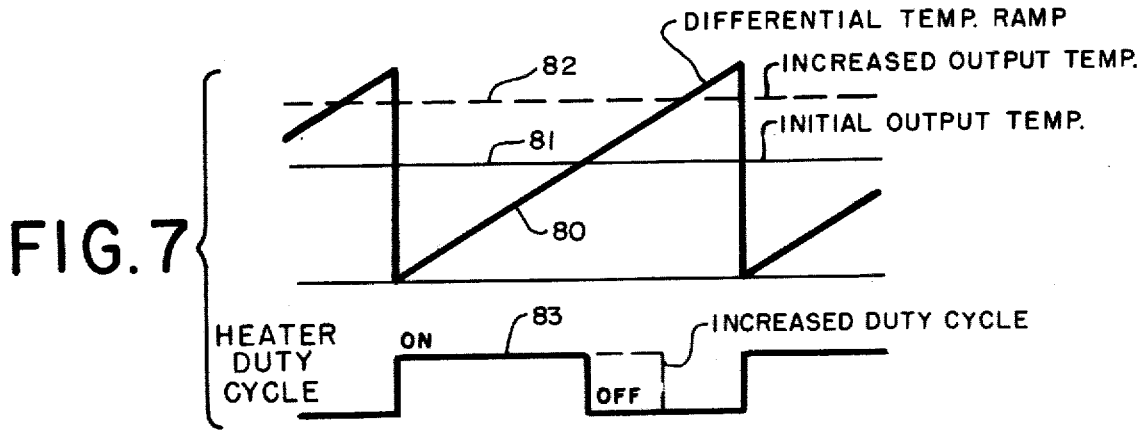
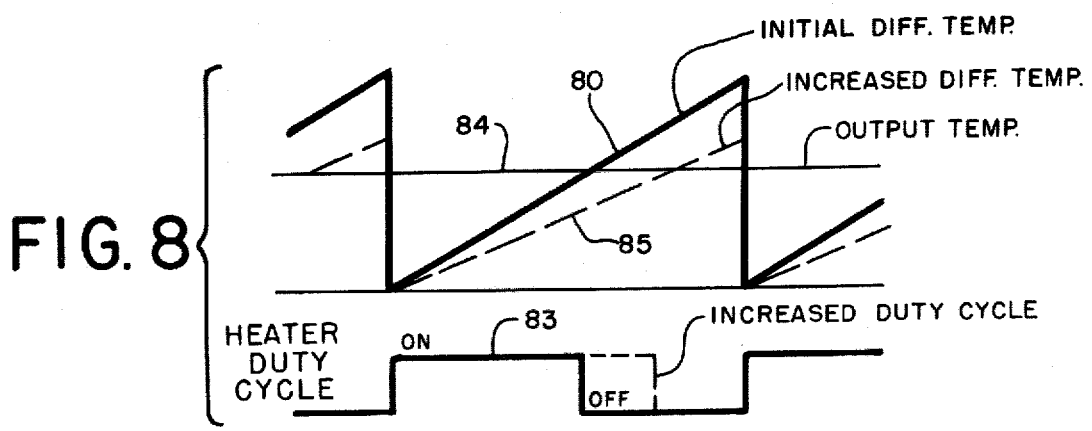

BLOOD WARMING APPARATUS WITH DIGITAL DISPLAY AND MONITORING CIRCUIT

BACKGROUND OF THE INVENTION

This invention is directed generally to fluid warming apparatus and, more particularly, to a monitoring circuit for use in apparatus for warming parenteral fluids such as whole blood for intravenous injection or transfusion procedures.

Whole blood is commonly stored in blood banks at a reduced temperature in the order of 4° C. To prepare this blood for infusion into a patient, it is necessary that the blood be warmed to the temperature of the human body, which is nominally 37° C. For applications where substantial and unpedictable quantities of blood may be required, such as where a patient hemorrhages during surgery, it is preferable that the blood be transferred from storage directly to the patient, since this avoids warming blood which is not subsequently used.

One effective and efficient apparatus for dry warming blood or other parenteral fluids to body temperature during the process of infusing such fluids into the patient is described in the copending application of Baxter Travenol Laboratories, Inc., Ser. No. 761,926, filed Jan. 24, 1977. It is a feature of this apparatus that the temperature of the infused blood is maintained constant at 37° C. substantially independently of flow rates, which may vary from 0 tp 150 ml per minute depending on the needs of the patient. Sterility of the blood is maintained and contamination of the apparatus is avoided by use of a disposable flow system having a blood warming bag which fits within the apparatus in thermal communication with electric heating elements.

The present invention is directed to a monitoring circuit which, when incorporated in the apparatus, provides both a digital indication of blood temperature and constant protection against overtemperature operation independent of the control circuitry of the apparatus. By reason of its novel construction, the monitoring circuit is incorporated in the apparatus with minimal changes to existing circuitry.

Accordingly, it is a general object of the present invention to provide new and improved apparatus for warming blood and other parenteral fluids prior to infusion into the human body.

It is another object of the present invention to provide a new and improved monitoring circuit for apparatus for warming blood and other parenteral fluids prior to infusion into the human body.

It is another object of the present invention to provide a new and improved monitoring circuit for a blood warming apparatus which provides improved protection against malfunction of the apparatus.

It is another object of the present invention to provide a new and improved blood warming apparatus which provides a digital temperature readout of improved accuracy.

SUMMARY OF THE INVENTION

The invention is directed to a monitoring system for use in fluid warming apparatus of the type which heats a refrigerated fluid such as blood to a predetermined nominal temperature at flow rates variable over a substantial predetermined range, and which includes a housing defining a heating chamber for the fluid within the apparatus, the fluid having an input temperature at the input of the chamber and an output temperature at the output of the chamber; means including at least one electric heater element operable from an applied electric current in thermal communication with the fluid in the heating chamber for heating the fluid as it passed through the chamber; control circuit means responsive to the input and output temperatures for generating a heater control signal dependent on both the output temperature and the flow rate of the fluid through the chamber; and switch circuit means electrically connected between the heating element and a source of electrical current, and response to the heater control signal, for controlling the application of current to the heating element, to maintain the fluid at the predetermined nominal temperature notwithstanding variations in the flow rate thereof. The monitoring system comprises temperature sensing means for generating an analog output signal indicative of the output temperature of the blood; conversion means for converting the analog output signal to a digital output signal; indicator means responsive to the digital output signal for displaying the output temperature of the fluid; and alarm generator means responsive to the digital output signal for generating an alarm upon the output temperature of the fluid exceeding a predetermined maximum level.

In a preferred construction of the invention, the conversion means comprise a multiplexed analog to digital converter having a serial binary data output and a strobe output; the indicator means comprise a plurality of display panels enabled by the strobe signal to respond to respective ones of the binary data output signals, and the alarm generator means is enabled by the strobe means to respond to only a selected one of the serial digital data signals.

In a preferred construction of the invention the temperature sensing means comprises a thermistor in thermal communication with the fluid at the outlet of said chamber, the indicator means is linearly responsive to an applied voltage signal and includes an input terminal, and the temperature sensing means comprise a constant-current source, the thermistor, and first and second resistances; the constant current source being coupled to one terminal of the thermistor and being connected to a plane of reference potential through the first resistance; the input terminal being coupled to the other terminal of the thermistor and to the plane of reference potential through the second resistance.

BRIEF DESCRIPTION OF THE DRAWINGS

The features of the present invention which are believed to be novel are set forth with particularlity in the appended claims. The invention, together with the further objects and advantages thereof, may best be understood by reference to the following description taken in conjunction with the accompanying drawings, in the several figures of which like reference numerals identify like elements, and in which:

FIG. 5 is a simplified functional block diagram of the blood warming apparatus showing the principal control elements thereof;

FIG. 7 is a graphical depiction of the operation of the blood warming apparatus illustrating the effect of variations in blood output temperature on the duty cycle of the heating elements contained therein;

FIG. 8 is a graphical depiction of the operation of the blood warming apparatus illustrating the effect of variations in flow rate on the duty cycle of the heating elements contained therein;

DESCRIPTION OF THE PREFERRED EMBODIMENT

Figure 2:
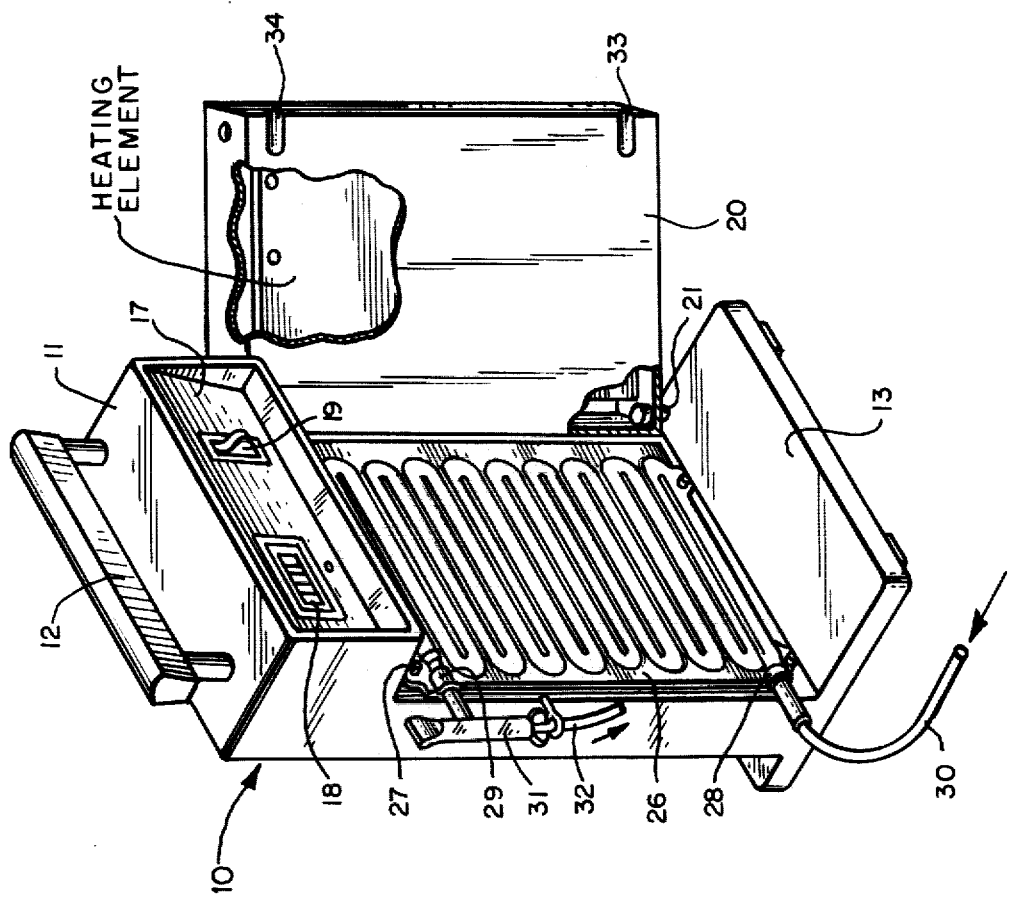
FIG. 2 is a perspective view of the blood warming apparatus with its heating chamber access door open and partially broken away to show the internal placement of the blood warming bag of the flow system.

Referring to the Figures, and particularly to FIGS. 1-4, a blood warming apparatus 10 constructed in accordance with the invention is seen to comprise a generally rectangular housing 11 having a handle portion 12 at its top end and a base portion 13 at its bottom end. In use, the blood warming apparatus can either be set on a flat supporting surface, as shown in FIG. 2, in which case the wide base portion 13 provides a high degree of stability, or can be mounted on a vertical support or IV pole 14, as in FIG. 1, wherein a pair of clamps 15 and 16 provided on the rear surface of the apparatus provide the necessary stability.

The blood warming apparatus is also seen to include in the upper portion of its housing a control panel 17, which may be slightly recessed for protection while the apparatus is in transit and storage. The control panel includes temperature indicating means in the form of a digital readout panel 18 which provides a readout of blood output temperature, and an ON-OFF power switch 19 which allows the operator to initiate and terminate operation of the apparatus.

The blood warming apparatus 10 includes under panel 17 a heater compartment access door 20 which is pivotably mounted on pins 21 (FIG. 2) to housing 11 at one end so as to open as shown in FIG. 2, providing access to a heating chamber 24 (FIG. 3) formed within the apparatus between the inside wall or plate 22 of the door 20 and the underlying wall or plate 23 of housing 11.

Figure 1:
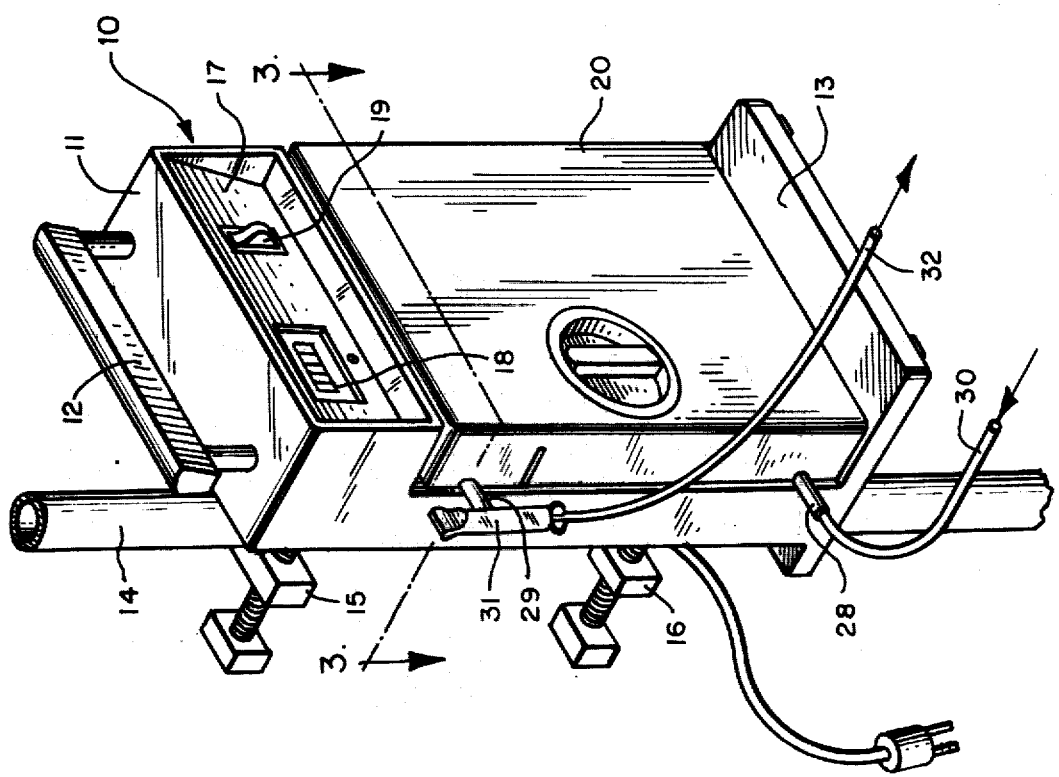
FIG. 1 is a perspective view of a blood warming apparatus incorporating the invention and having a disposable blood warming flow system installed therein.

The blood warming apparatus is intended for use in conjunction with a sterile disposable fluid flow system through which whole blood or other fluids to be warmed are caused to flow, either by means of gravity or pressure feed, to a patient or other destination. One such flow system is marketed by Fenwal Laboratories, a division of Baxter Travenol Laboratories, Inc., of Deerfield, Ill., U.S.A., as model No. 4C2416, and is intended for infusing blood from a storage container directly to a patient. The flow system includes a flat generally rectangular warming bag 26 (FIG. 2) which is suspended within chamber 24 by means of a plurality of support pins 27. The warming bag 26 is internally baffled to define a tortuous flow path 25 (FIG. 4) for the blood as it flows from an inlet port 28 at the lower end of the bag to an outlet port 29 at the upper end of the bag. Inlet port 28 is connected by a length of tubing 30 to a container of refrigerated blood (not shown), and outlet port 29 is connected through a chamber 31 and a length of tubing 32 to a needle adapter (not shown), to which a needle is attached for venipuncture. When access door 20 is closed as shown in FIG. 1, the blood warming bag 26 is sandwiched between plate 22 of door 20 and plate 23 of housing 11, and connection is established to inlet and outlet ports 28 and 29 through recesses 33 and 34, respectively, provided along the edges of the door and housing. These recesses allow the door to be closed snugly over the warming bag.

Figure 3:
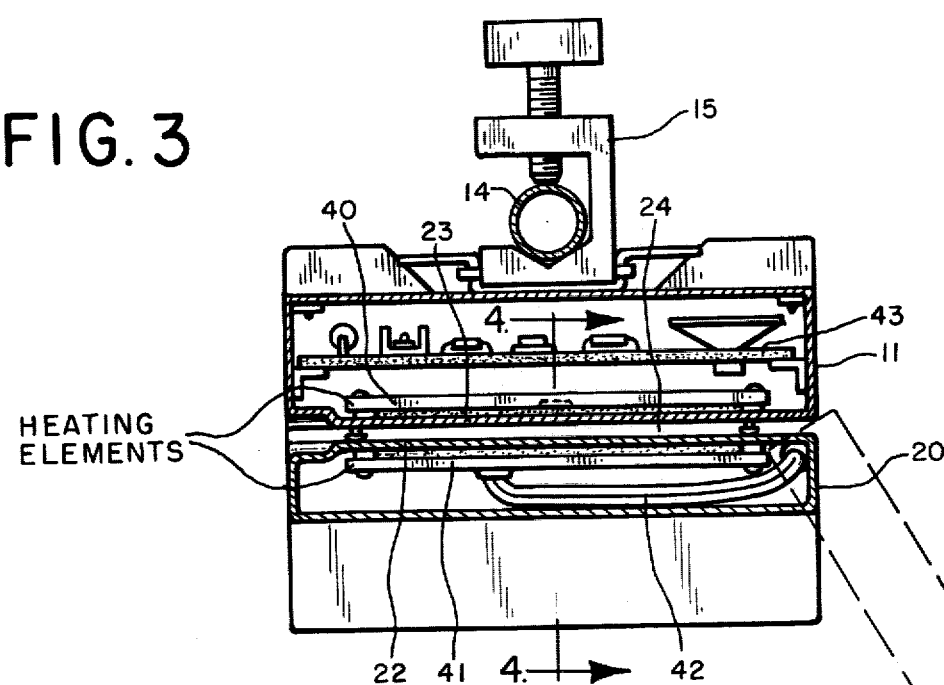
FIG. 3 is a cross-sectional view taken along line 3—3 of FIG. 1 showing the interior construction of the blood warming apparatus.

Referring to FIG. 3, to warm the blood flowing through warming bag 26 the blood warming apparatus includes a first heating element 40 within housing 11 in substantially contiguous contact with the inside surface of plate 23. A second heating element 41 is positioned within door 20 immediately behind and adjacent to the inside plate 22 of the door. Electrical power is supplied to heating element 41 by means of electrical conductors 42 which extend into the interior of housing 11 through the upper pivot hinge 21 of door 20. Electrical components and circuitry, including a printed wiring board 43 necessary for operation of the blood warmer apparatus, are contained within housing 11 behind heating element 40.

Figure 4:
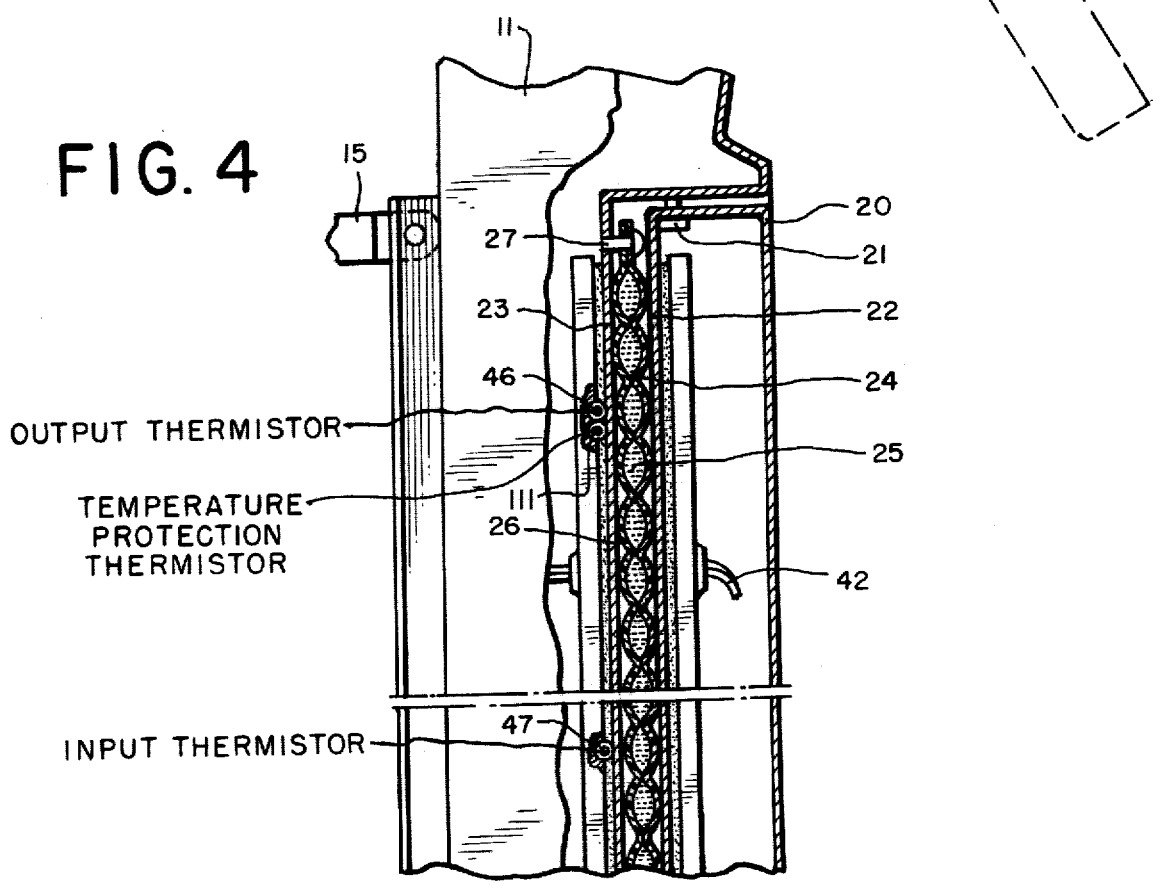
FIG. 4 is a cross-sectional view taken along line 4—4 of FIG. 3 showing the placement and construction of the heating elements of the blood warming apparatus and the placement of the blood temperature sensing elements provided therein.

Referring to FIG. 4, when access door 20 is closed blood warming bag 26 is sandwiched between plates 22 and 23 so that blood flowing through the interior passageways 25 of the warming bag comes into thermal communication with heating elements 40 and 41. The temperature of the blood flowing through the blood warming bag is sensed by temperature sensing means in the form of a pair of thermistors 46 and 47 located on the center line of recess 24 near the top and bottom of the recess. Thermistor 47 measures the temperature of the blood flowing through the warming bag near inlet port 28, and thermistor 46 measures the temperature of the blood in bag 26 near outlet port 29. Within the blood warming apparatus thermistors 46 and 47 provide analog signals indicative of the temperature of the blood discharged from the apparatus as well as the differential temperature which exists between the blood entering the apparatus and the blood being discharged. This information is utilized by control circuitry within the apparatus to control the operation of heating elements 40 and 41, and consequently the temperature to which the blood is heated.

Referring to the simplified functional block diagram of FIG. 5, the temperature of the blood discharged from the blood warming apparatus 10 is controlled by means of a heater duty cycle control circuit 50 which causes the heating elements 40 and 41 to be periodically energized with a duty cycle dependent on the temperatures sensed by thermistors 46 and 47. The output of this circuit, which comprises a heater on-off control signal, is applied through an optical isolator 51 to a heater switch circuit 52, which controls application of current to heater elements 40 and 41. Current for powering heaters 40 and 41 is supplied to heater switch circuit 52 from the AC line through a circuit breaker 53 which also functions as a user-actuable power switch and a means of automatically disconnecting power to the unit in the event of a malfunction. Optical isolator 51, which comprises a conventional commercially available component, functions to electrically isolate duty cycle control circuit 50 from the switched AC line and the other control circuits of the blood warming apparatus to minimize leakage between the AC line and the patient under treatment.

The heater duty cycle control circuit 50 varies the duty cycle of heaters 40 and 41 both as a function of the output temperature sensed by sensor 46, and as a function of the differential between the input and output temperature of the blood as sensed by sensors 46 and 47. As the output temperature of the blood increases beyond the desired level control circuit 50 functions to reduce the duty cycle of heaters 40 and 41, thus lowering the output temperature to the desired level. Conversely, as the output temperature of the blood decreases below the desired level control circuit 50 functions to increase the duty cycle of the heaters, thus increasing the blood temperature to the desired level. At the same time, should the differential in sensed temperatures increase, signifying an increase in blood flow rate, the duty cycle of heaters 40 and 41 is automatically increased to compensate for the increased flow rate and avoid the output temperature of the blood falling below the desired level. Conversely, as the difference between the sensed input and output temperatures decreases, signifying a reduced flow rate, the duty cycle of the heaters is automatically reduced to avoid heating the blood beyond the desired level.

Protection is provided against malfunction of the control circuit by means of a first alarm circuit comprising an over-under temperature monitor circuit 54 which provides an output in the event that the blood output temperature, as sensed by sensor 46, rises above a predetermined maximum temperature or falls below a predetermined minimum temperature. In practice, the maximum temperature limit is set just slightly above the nominal body temperature to 37° C. to avoid any possibility of damage to the blood being processed, and the minimum temperature limit is set at approximately 0° C. so as to sense a failure of the output temperature sensor 46.

In the event of an output from temperature monitor 54 indicating either an over or under temperature condition, an alarm 55 is actuated to indicate to the user that a malfunction has occurred. Simultaneously, the application of control signals from control circuit 50 to the heater switch circuit 52 is interrupted to prevent further heating of the blood by heating elements 40 and 41.

The blood warming apparatus 10 incorporates a second monitoring circuit 56 which monitors current supplied to heating elements 40 and 41. During normal operation this current is periodically switched on and off at a rate determined by control circuit 50. Should a malfunction occur which results in a continuous current being applied to heaters 40 and 41, duty cycle monitor 56 generates an output signal which is applied to an appropriate terminating device in circuit breaker 53 to interrupt power to the blood warming apparatus. In practice, duty cycle monitor 56 is constructed to terminate operation whenever power to the heating elements is not interrupted in a 3 second interval.

A further feature of the control arrangement shown in FIG. 5 is that power to the heating element is switched on only during those portions of the applied AC line current when that current is passing through its zero axis. This is done to minimize transients which would otherwise be generated by switching during periods of current flow through the heating elements, and to minimize the attendant radio frequency interference produced as a result of such transients.

Figure 6:
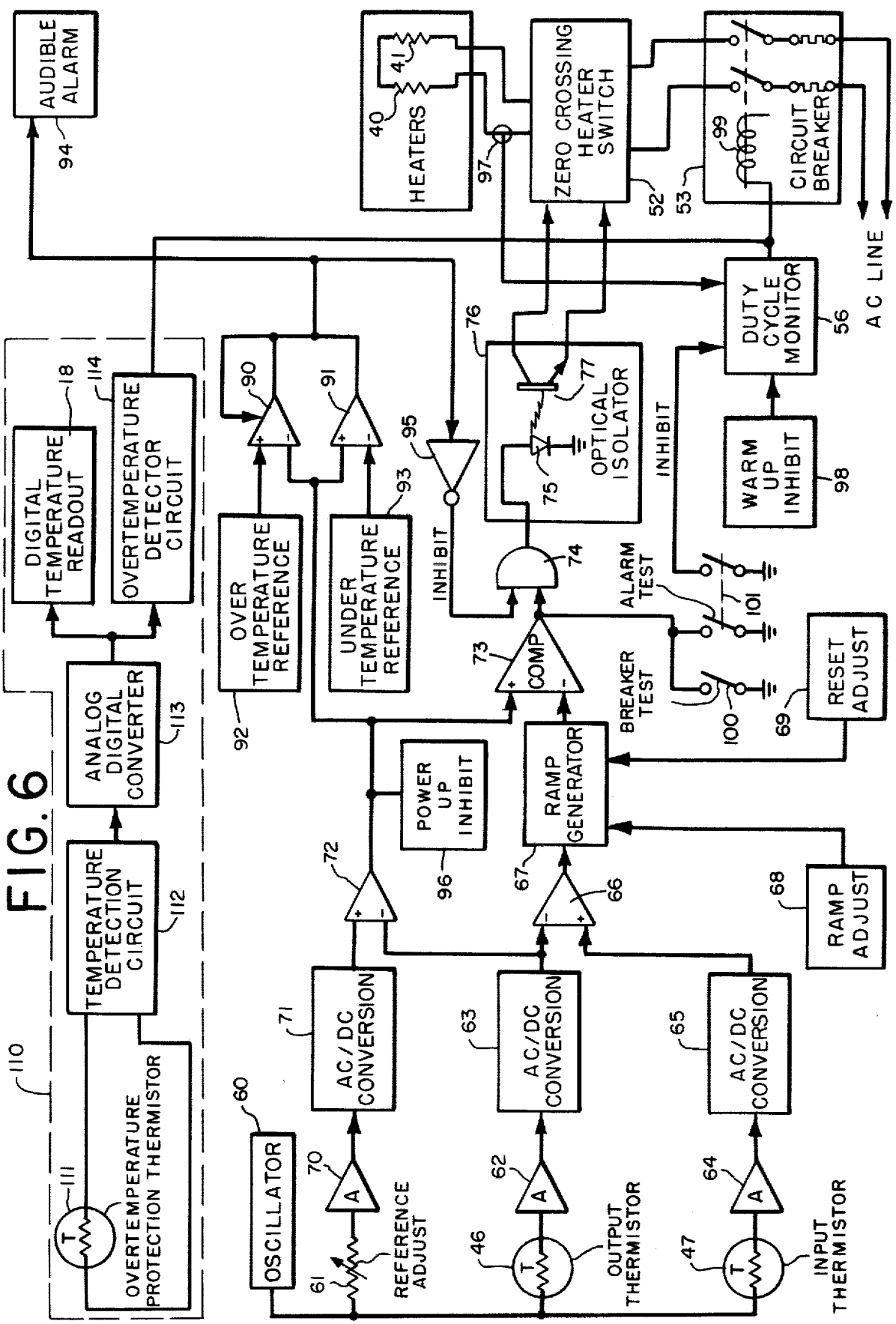
FIG. 6 is a functional block diagram of the blood warming apparatus showing the functional elements thereof.

As fully described in the previously identified application Ser. No. 761,926, the heater control signal applied to heater switch circuit 52 is generated within control circuit 50 by means of a slope-intercept system. Basically, as shown in FIG. 6, control circuit 50 includes an oscillator 60 which generates a square wave signal at approximately 2 kilohertz. This signal is simultaneously applied to thermistors 46 and 47 and to a reference-adjust potentiometer 61. Thermistor 46 provides at the input of an amplifier 62 a square wave signal amplitude-dependent on the output temperature of the blood being processed. This signal is amplified in amplifier 62 and applied to an AC-DC conversion stage 63 wherein it is converted to an analog signal indicative of the output temperature of the blood. Similarly, thermistor 47 develops a variable-amplitude square wave signal which is amplified in an amplifier 64 and converted to an analog temperature-indicative signal in an AC-DC conversion stage 65.

The analog signals from conversion stages 63 and 65 are applied to the inverting and non-inverting inputs of a first differential amplifier 66 which produces an output signal indicative of the difference between the two applied signals. This output signal is applied to a ramp generator 67 which generates repetitive ramp voltage functions each having a slope which varies inversely with the amplitude of the applied signal. Ramp generator 67 includes a circuit provision 68 for setting the initial slope of the ramp in the absence of an applied differential signal, and a circuit provision 69 for establishing the reset voltage level at which point the ramp generator recycles. In practice, the slope of the ramp and the recycle level are such that the ramp function is repeated nominally every 600 milliseconds. This is a relatively long control period relative to the 16.7 millisecond period of the 60 hertz AC line which supplies current to the heating elements and must be switched on and off, and a relatively short period compared to the thermal inertia of the blood warming apparatus so as not to constitute a limiting factor in system performance.

The reference-adjust potentiometer 61 provides a square wave signal of adjustable amplitude which once set varies only with variations in the amplitude of the square wave signal produced by oscillator 60. This signal is amplified in an amplifier 70 and applied to an AC-DC conversion state 71, wherein it is converted to a temperature-dependent oscillator amplitude-dependent analog signal. This analog signal is applied to the non-inverting input of a second differential amplifier 72. The analog signal from conversion stage 63 is applied to the other inverting input of amplifier 72 to develop an output signal therefrom which constitutes an output temperature-indicative signal independent of amplitude variations in oscillator 60.

The output temperature-indicative signal from differential amplifier 72 is applied to the non-inverting input of a voltage comparator 73, and the variable-slope repetitive ramp function generated by ramp generator 67 is applied to the inverting input of this comparator. As the instantaneous voltage level of the ramp function increases with time, a point is eventually reached at which the ramp and temperature-indicative functions become equal. At this point an output is produced by comparator 73 which constitutes the desired heating element control signal.

The heater control signal is applied to one input of an AND gate 74. The output of this gate is applied to a light emitting diode (LED) 75 which preferably comprises an integral element of a conventional optical isolator component 76. Within isolator 76 the light emitted by LED 75 establishes conduction in an optically associated semiconductor device 77. The semiconductor device is connected to the zero crossing heater switch 52 such that when conductive it conditions the switch to a conductive state to energize heating elements 40 and 41.

Since an output is developed by comparator 73 only when the voltage levels applied to its inputs are equal or of a positive relationship, the duty cycle of the output signal developed by the comparator is dependent on both the absolute temperature of the discharged blood, as signified by the analog signal applied from differential amplifier 72, and the difference between the input and output blood temperatures, is signified by the slope of the repetitive ramp voltage function applied from ramp generator 67. This is illustrated in FIGS. 7 and 8. In FIG. 7 it is seen that the waveform 80 representing the ramp function generated by ramp generator 67 for a constant temperature differential intersects the lower voltage level 81 corresponding to an initial output temperature sooner than it intersects a voltage level 82 corresponding to an increased output temperature. As a result the heater-on duty cycle, as depicted by waveform 83, is increased with increased voltage levels accompanying decreases in blood output temperature.

The effect of variations in temperature differential is illustrated in FIG. 8. For an initial differential temperature the waveform 80 of the ramp function intersects the voltage level 84 corresponding to the blood output temperature and terminates the heating cycle earlier than when the slope has decreased because of an increased temperature differential, as shown by waveform 85. The result is that the duty cycle of the heater, as depicted by waveform 83, increases to enable the blood warming apparatus to accomodate the increased flow rate which brought about the increased temperature differential.

In practice, both temperature differential and blood output temperature vary with time, and the resulting duty cycle is a composite of both of these variables. Of particular advantage is the fast response time this circuit arrangement provides compared to thermostatically-controlled blood warming apparatus wherein the heater elements were energized only on demand.

The temperature of the discharged blood is continuously monitored by means of a high and low limit comparison circuit formed by differential amplifiers 90 and 91. The temperature-indicative output signal from differential amplifier 72 is applied to the inverting input of differential amplifier 90, and a reference signal developed in an over-temperature reference source 92 is applied to the non-inverting input of this device. The output of amplifier 90 includes a feedback network so that when the measured temperature exceeds the over-temperature reference, amplifier 90 is locked in an on state until subsequently reset by removal of power from the apparatus.

The output of differential amplifier 72 is also coupled to the non-inverting input of differential amplifier 91, the inverting input of which is connected to an under-temperature reference voltage source 93. The output of this amplifier is coupled to the output of amplifier 90, so that if the voltage level developed by differential amplifier 72 falls below that from reference 93 an output is developed from amplifier 91 which locks amplifier 90 in an on state as if that amplifier had detected the over-temperature condition. Thus, upon occurrence of either an over-temperature or under-temperature condition, an output is developed which remains until power is removed from the apparatus.

The alarm signal from amplifiers 90 and 91 is applied to an alarm 94 which sounds an audible alarm to alert the user that the blood output temperature is out of limits.

The alarm signal developed by differential amplifiers 90 and 91 is also applied through an inverter 95 to the remaining input of AND gate 74 to inhibit that gate upon occurrence of an alarm condition. Since inhibiting this gate has the effect of preventing actuation of the heater control signal to optical isolator 76 and heater switch 52, the application of power to heating elements 40 and 41 is terminated. A power-up inhibit circuit 96 provides an alarm inhibiting voltage at the output of amplifier 72 for a short period of time, typically in the order of a few seconds, upon initial operation of the blood warming apparatus to prevent actuation of the temperature alarm.

As previously stated, the duty cycle monitor 56 monitors the AC current applied to heater elements 40 and 41 to ascertain the correct functioning of the heater control circuit 50, optical isolator 76, and zero-crossing heater switch 52. This monitoring is accomplished by means of a current probe 97 to avoid a direct electrical connection between the monitor circuit and the AC line.

Since the monitor produces an output only in the event that power to the heaters is not interrupted over a three second interval, and the nominal duty period of the heaters is 600 milliseconds, the monitor normally will only actuate in the event of a malfunction. However, during initial operation of the blood warming apparatus it is possible, particularly when the apparatus is cold, that the duty cycle control circuit will as a result of sensing a low output temperature call for continuous operation of the heater elements. To prevent the duty cycle monitor 56 from interpreting this normal warm-up mode of operation as a fault, the blood warming apparatus preferably includes a warm-up inhibit circuit 98 which inhibits the operation of the duty cycle monitor for a predetermined time period following initial power up of the apparatus. Typically, this time period is set at approximately two minutes, which has been found adequate to bring plates 22 and 23 up to operating temperatures in even abnormally cold conditions.

After the initial warm-up period has passed, and duty cycle monitor 56 detects a fault, a signal is applied to a solenoid 99 associated with circuit breaker 53 to trip the circuit breaker to an open condition, thus removing all power from the blood warming apparatus. It will be observed that the circuit breaker 53 of the apparatus can be tripped in three ways; (1) manually by the user, (2) electrically by solenoid 99, and (3) by a short circuit or ground fault within the apparatus or heater elements causing the breaker to trip as a result of the ensuing overload.

The heater elements 40 and 41, which preferably comprise 368 watt pad-type units, are preferably connected in series so that should one element become open the other element will be rendered inoperative.

To provide a positive test of the operability of the various monitoring circuits, the blood warming apparatus preferably includes a breaker test function initiated by a push button switch 100 on the rear panel of housing 11. Actuation of this switch causes a continuous signal to be applied to optical isolator 76, and hence to heater switch 52. Since this results in heater elements 40 and 41 being continuously powered, if duty cycle monitor 56 is operative a control signal will be developed after approximately two minutes which will trip circuit breaker 53 and cause power to be removed from the blood warming apparatus.

To provide a test of the apparatus alarm circuitry, the blood warming apparatus includes an alarm test function which is initiated by a push button switch 101 located on the rear panel of housing 11. This switch, when actuated, causes a continuous current to be applied to the heater elements, while at the same time inhibiting the duty cycle monitor 56. Now, circuit breaker 53 is not tripped and the heaters remain energized to raise the temperature of the heating elements until the temperature of the elements becomes greater than the upper limit temperature set by reference 92. At this point differential amplifier 90 is locked to an on state, generating an output signal which actuates alarm 94 and inhibits AND gate 74 to remove power from the heating elements. Thus, the blood warming apparatus includes provisions for testing its internal monitoring circuitry to assure that a malfunction of the heater control circuitry will not result in delivery of blood outside of a desired temperature range.

In accordance with the invention, the blood warming apparatus 10 additionally includes a combined overprotection and digital indicator monitoring circuit 110 which operates independently of the previously described control and protection circuitry of the apparatus. Basically, as shown in FIG. 6, this monitoring circuit utilizes an additional thermistor 111 positioned adjacent the output temperature sensing thermistor 47 to sense the output temperature of the blood as it leaves the blood warming apparatus. Thermistor 111 functions in conjunction with a temperature detection circuit 112 to develop an analog output signal indicative of the temperature of the blood as it leaves the blood warming apparatus. This analog signal is applied to an analog to digital converter 113 wherein it is converted to a corresponding signal of binary form. The binary signal is applied to the digital temperature readout device 18 of the apparatus, which responds by displaying the temperature in digital form to the user. The digital signal is also applied to an over-temperature detector circuit 114, wherein it is analyzed to determine if the operating temperature is below a predetermined maximum limit. Should the temperature be out of limit, i.e. exceed the safe maximum operating temperature of the apparatus, then a control signal is developed which is applied to solenoid 99 to actuate circuit breaker 53 to an off position.

In this way, the blood warming apparatus monitor system independently monitors the operation of the blood warming apparatus, providing a digital display to the operator at all times, and interrupting operation in the event of over-temperature operation.

Figure 9:
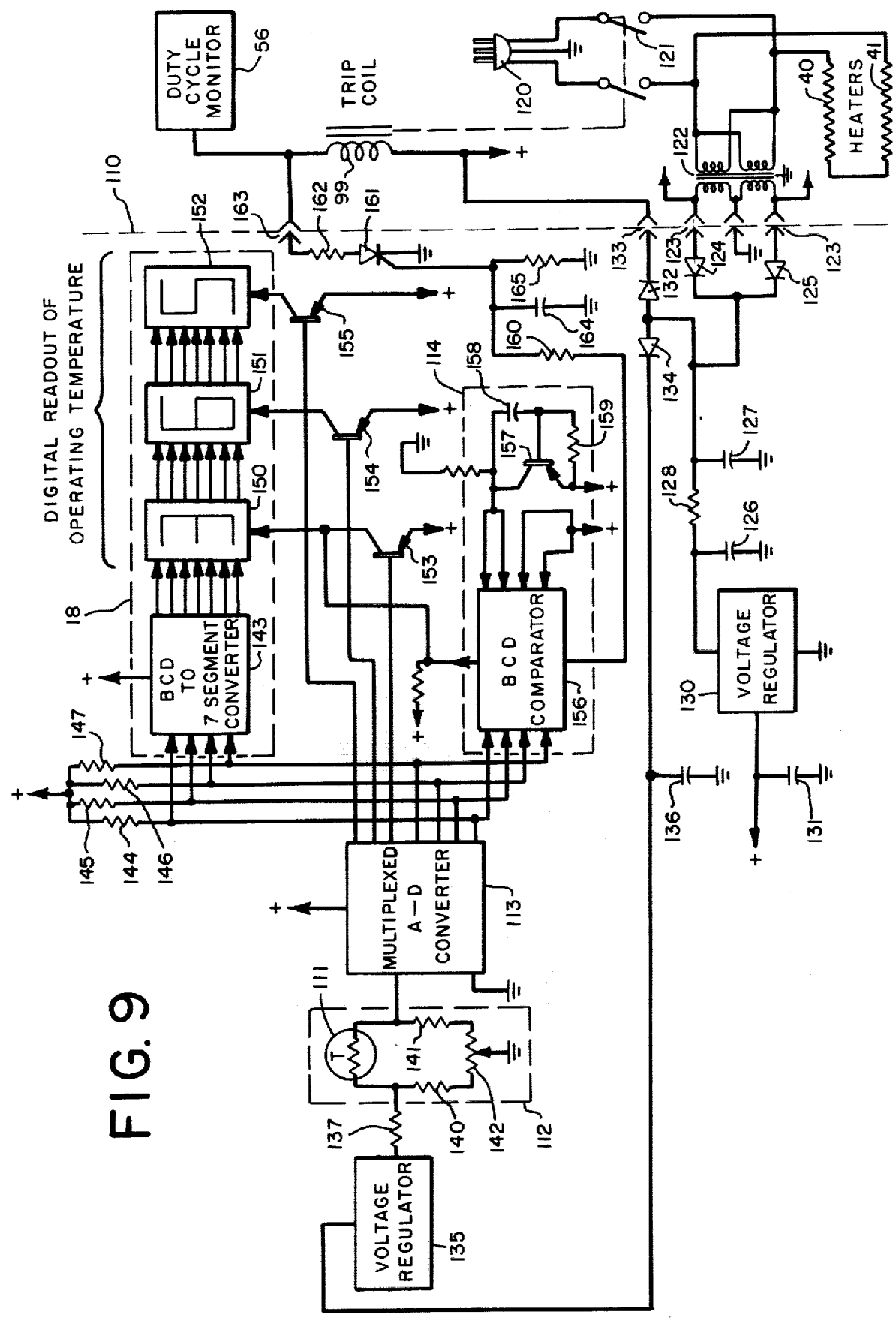
FIG. 9 is a simplified schematic diagram, partially in functional block form, of the digital monitoring circuitry of the blood warming apparatus.

The monitoring circuit is shown in greater detail in FIG. 9. There it is seen that AC power is supplied to blood warming apparatus 10 through a conventional three-pronged grounded plug 120. The plug is connected through contacts 121 to the primary windings of a transformer 122, which is utilized to provide operating power for the various control and monitoring circuits of the blood warming apparatus. Contacts 121, which comprise a portion of circuit breaker 53, are also connected to heaters 40 and 41, so that the latter elements are powered as long as contacts 121 are closed.

The secondary windings of transformer 122, in addition to connecting with conventional power supply circuitry associated with the control circuits, are also connected through connecting pins 123 to respective diodes 124 and 125 of a power supply circuit associated with the temperature monitoring circuit 110. The center cap of the secondary winding is grounded, and the cathodes of diodes 124 and 125 are connected to a filter network comprising a pair of capacitors 126 and 127 and a resistor 128 which function as a filter network to reduce the ripple component in the resulting direct current in a manner well known to the art. The filtered output from this network is applied to a voltage regulator 130 which provides a regulated voltage source for the individual components of the monitor circuit. An additional filter capacitor 131 connected between the output of regulator 130 and ground provides additional filtering action.

The direct current output of diodes 124 and 125 is also applied through a diode 132 and connector pin 133 to solenoid 99 to serve as an alternate source of energization for that component. The direct current output is also applied through a second isolation diode 134 to a second voltage regulator 135 of the monitor circuit. An additional filter capacitor 136 provides additional filtering for the direct current thus applied.

The voltage-regulated output of voltage regulator 135 is applied through a resistor 137 to a detector circuit 112, which comprises a thermistor 111, a pair of resistors 140 and 141, and a potentiometer 142. Resistor 140 is connected between one terminal of thermistor 111 and potentiometer 142, and resistor 141 is connected between the other terminal of thermistor 111 and potentiometer 142. The arm of the potentiometer is grounded. The other terminal of thermistor 111 is connected to one input terminal of the analog-to-digital converter 113. The other input terminal of this converter is connected to ground.

Converter 113 is preferably a multiplexed type converter which responds to a low-level analog input signal to produce a binary coded decimal (BCD) signal in serial-digit form, together with necessary control signals for sequentially displaying the individual digital signals. This type of converter is well known to the art, and is available in several commercial versions. One such version is marketed by Analog Devices of Norwood, Masschusetts as part number AD2020. Another such device is marketed by RCA as part number CA3162E.

The BCD output of converter 113 is applied to a BCD-to-7 segment converter in indicator unit 18. This converter, which may be conventional in design and construction, converts the BCD signal to a seven segment output signal suitable for controlling the operation of individual seven segment indicator panels such as are commonly used for digital display purposes. Individual resistors 144-147 connect the individual BCD outputs of converter 113 to a source of positive potential current to provide necessary bias at the inputs of the converter. The seven individual control signals produced by converter 143 are simultaneously applied to each of three individual display devices 150-152 included in the display unit 18.

The operation of the individual display panels 150-152 is controlled by means of strobe signals produced by converter 113. Operating current is supplied to the three panels through respective ones of transistors 153-155. The strobe outputs of the multiplexed converter 113 are connected to respective ones of these control transistors, so that upon occurrence of a strobe signal the associated transistor is driven into saturation and the associated display panel is rendered functional. In this way, it is possible to activate the associated display panel only when the corresponding BCD signal appropriate to that panel is present at the output of converter 113. By producing the BCD signals appropriate to each digit of the indicated temperature in a regular sequence, and by producing strobe signals to activate the corresponding display panels in synchronism with this sequence, it is possible to display the output temperature by activating only one display panel at a time. In practice, the sequencing is done very quickly, so that it is not noticeable to the eye. This arrangement minimizes circuit complexity and power consumption.

Over-temperature protection is achieved by applying the serially occurring BCD output signals from converter 113 to a BCD comparator stage 156 incorporated in the over-temperature detector circuit 114. This comparator, which may be conventional in design and construction, is enabled upon occurrence of the strobe signal associated with the most significant digit of the digital output signal, in this case the tens digit, to compare the then existing BCD output signal from converter 113 with a fixed BCD "3" signal formed by connecting the least significant digits of the fixed input to a positive current source. Should the applied BCD signal be greater than "3", corresponding to an operating temperature of 40° C. or above, an output signal is produced by the comparator.

To inhibit operation of the comparator upon initial power-up of the blood warming apparatus, the two most significant of the fixed BCD inputs to comparator 156 are connected to a positive polarity unidirectional current source by a transistor 157. The base of this transistor is connected through a capacitor 158 to the two input terminals, and by a resistor 159 to the positive polarity unidirectional current source. Upon initial power-up of the apparatus transistor 157 is saturated as capacitor 158 charges, momentarily forcing a BCD "15" into the comparator input. Since the output of converter 113 is incapable of exceeding a BCD "15", the comparator is momentarily prevented from indicating an over temperature condition until transistor 158 becomes non-conductive allowing the apparatus time to stabilize.

After the warm-up period, when the BCD output of converter 113 becomes equal to or greater than the fixed BCD input at comparator 156, the output signal produced by the device is applied through a resistor 160 to the gate electrode of a silicon controlled rectifier (SCR) 161. The cathode of SCR 161 is grounded, and the anode is connected through a resistor 162 to the trip coil 99 of circuit breaker 53. The applied signal from comparator 156 drives the SCR into saturation, allowing trip coil 99 to be actuated by current flow through resistor 162. Since trip coil 99 can be supplied with current from either the blood warming apparatus power supply, or from the monitor circuit power supply comprising diodes 124 and 125, actuation of the circuit breaker is assured even upon failure of either one of the power supplies. A short time delay is introduced into the gate circuit of SCR 161 by parallel-connected capacitor 163 and resistor 164 to prevent actuation of SCR 161 from extraneous noise sources, and to this end the time constant of this network is selected so that a continuously occurring output signal comparable to the duration of the strobe signal from converter 113 is necessary before the gate threshold of SCR 161 will be exceeded.

Figure 11:
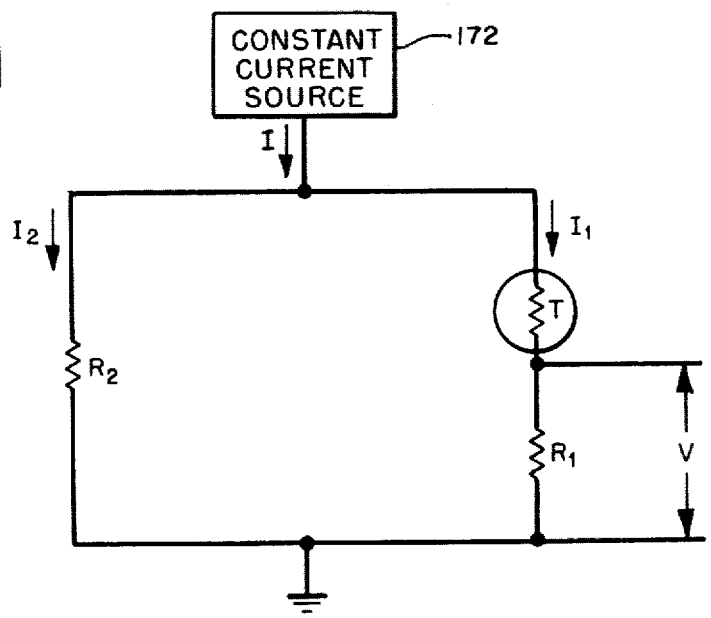
FIG. 11 is a schematic diagram of the coupling circuit utilized in the digital monitoring circuitry of the invention.

To achieve an accurate indication of blood temperature, it is imperative that a linear relationship exist between the measured temperature of the blood and the voltage applied to converter 113 over the normal operating range of the blood warming apparatus. To this end, the additional thermistor 111 of the monitoring circuit is connected to the input terminals of converter 113 by means of detection circuit 112, the electrical equivalent of which is illustrated in FIG. 11. Referring to FIG. 11, thermistor Rt is seen to be connected in series with a fixed resistance $R_1$ between a constant current source 172 and a plane of reference potential, or ground. The constant current source is also connected by a second fixed resistor $R_2$ to ground. One input terminal of converter 113 is connected to the juncture of thermistor $R_T$ and resistor $R_1$ and the other input terminal of this device is connected to ground. A current I is seen to flow from the constant current source, a current $I_1$ is seen to flow through thermistor Rt and resistor $R_1$, and a current $I_2$ is seen to flow through the fixed resistor $R_2$.

Assuming the input impedance of converter 113 is sufficiently high that an insignificant current flows between its input terminals, the following basic relationships exist in the circuit of FIG. 11:

$$V = I_1 R_1$$
$$I = I_1 + I_2$$
$$I_2 R_2 = I_1(R_T + R_1)$$
$$\left(I - \frac{V}{R_1}\right) R_2 = \frac{V}{R_1}(R_T + R_1)$$

then,
$$R_1 = \frac{V(R_T + R_2)}{IR_2 - V}, \text{ and}$$
$$R_2 = \frac{V(R_T + R_1)}{IR_1 - V}, \text{ and}$$
$$IR_1 R_2 = V(R_1 + R_2 + R_T), \text{ a constant.}$$

Assuming it is desired to linearize the transferred characteristic between the temperature of thermistor $R_T$ and the voltage V supplied to converter 113 over a temperature range of $T_1$ to $T_2$, with corresponding voltages $V_1$ and $V_2$ and resistances $RT_1$ and $RT_2$, then:

$$V_1(R_1 + R_2 + RT_1) = V_2(R_1 + R_2 + RT_2), \text{ and}$$
$$R_1 + R_2 = \frac{V_2 RT_2 - V_1 RT_1}{V_1 - V_2}$$

This results in a transfer function:

$$V = I\left(\frac{R_1 R_2}{R_1 + R_2 + R_T}\right)$$

Thus, the sum of $R_1$ and $R_2$ is a constant based on the temperature-resistance characteristic of the thermistor over a selected range. For example, assuming that at 32° C. $RT_1$ equals 3701.5 ohms and the desired voltage $V_1$ is 0.32 volts, and that at 40° C. $RT_2$ equals 2663.3 ohms and the desired voltage $V_2$ is 0.40 volts, $R_1$ and $R_2$ can be selected as follows:

$$R_1 + R_2 = \frac{.40(2663.3) - .32(3701.5)}{.4 - .32} = 1489.5 \text{ ohms}$$

Assuming that at a given temperature, e.g. 36° C., the following parameters exist $V = 0.36$ volts
$R_1 + R_2 = 1500$ ohms
$R_T = 3133.5$ ohms, then the transfer function
$V = I\frac{R_1 R_2}{R_1 + R_2 + R_T}$ becomes
$IR_1 R_2 = .36(1500 + 3133.5) = 1668$, and
$V = \frac{1668}{1500 + R_T}$ Thus, the transfer function of the detector circuit is seen to be independent of the value of the constant current I.

Figure 10:
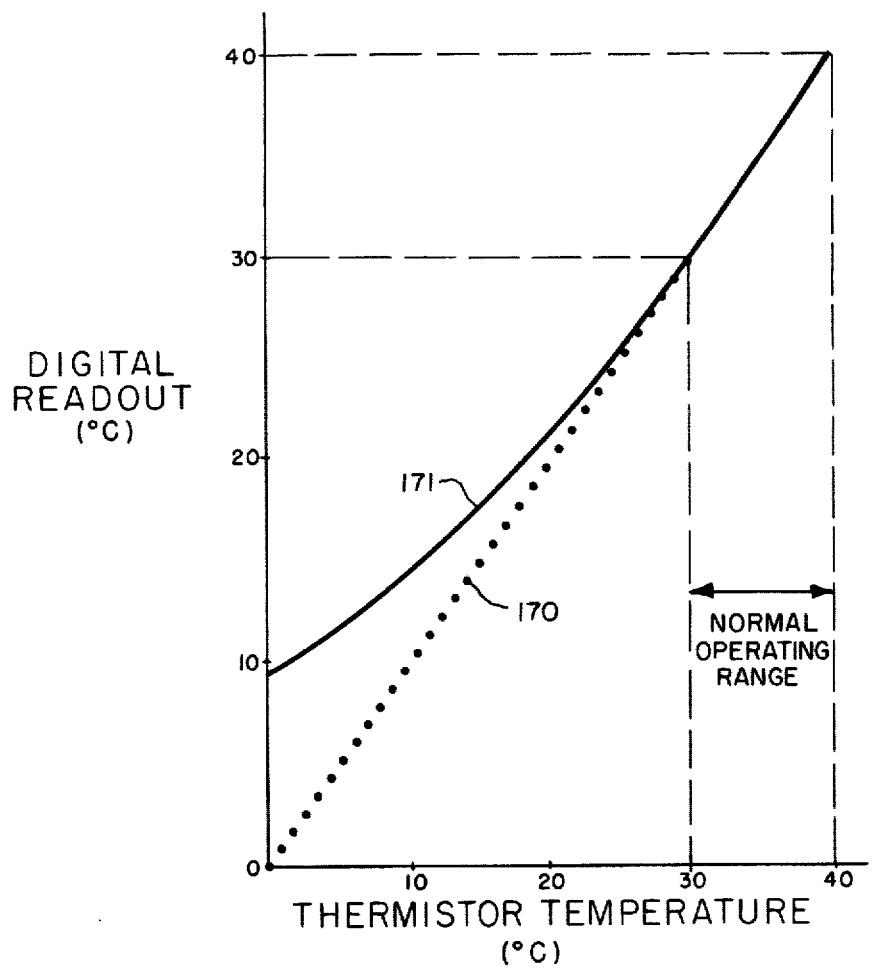
FIG. 10 is a graphical depiction of actual vs. indicated temperature useful in explaining the operation of the invention.

In practice, the circuit is linearized over an operating range from 30° C. to 40° C., which encompasses normal blood temperature of 37° C. As shown in FIG. 10, the transfer characteristic 171 of the circuit provides a high degree of linearity between displayed temperature and actual temperature in this range.

Commercially available devices suitable for use as the analog to digital converter 113 typically require applied voltages in the range of 0.3 to 0.4 volts to provide digital output indications in the range of 30° C. to 40° C., as illustrated in the foregoing examples. In practice, resistors $R_1$ and $R_2$ are provided by a single potentiometer 142 having a grounded arm, as shown in FIG. 9, thereby providing a constant total $R_1 + R_2$ resistance while allowing the ratio of $R_1$ and $R_2$ to be readily adjusted for a voltage V of 0.36 volts at a temperature of 36° C.

The resulting coupling network tracks temperature over a predetermined operating range (30° C.–40° C.) within a close tolerance (typically ±0.1° C.). The component values are not critical, and the circuit is independent of the selected level of the constant supply current I, as long as a minimum value of current is exceeded and the level of current does not vary with time or temperature.

The digital display and overtemperature monitor system of the invention provides a continuous highly accurate indication of operating temperature, and continuously guards against overtemperature operation. The circuit requires a minimal number of additional components, and requires minimal modification of the control circuitry of the blood warming apparatus. Should an overtemperature condition occur not corrected by the control circuitry of the apparatus, a trip coil is actuated to disable the application of power, irrespective of electrical malfunction in the apparatus itself.

It will be appreciated that while the invention is particularly well suited for heating blood, it also finds utility in other applications where a highly accurate fluid output temperature must be maintained over a wide range of flow rates, and that the nominal operating temperatures and time periods given by way of example in the blood warming application will change for such other applications.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

We claim:

1. Fluid warming apparatus for heating a refrigerated fluid such as blood to a predetermined nominal temperature, comprising:

a housing defining a heating chamber for the fluid
means including at least one electric heater element operable from an applied electric current in thermal communication with the fluid in said heating chamber for heating the fluid as it passes through the chamber;
control circuit means responsive to the output temperature of the fluid for generating a heater control signal;
switch circuit means electrically connected between said heating element and a source of electrical current, and responsive to said heater control signal, for controlling the application of current to said heating element to maintain the fluid at said predetermined nominal temperature;
temperature sensing means for generating an analog output signal indicative of the output temperature of said fluid, said temperature sensing means including an output terminal, a constant current source, a thermistor in thermal communication with said fluid at the output of said heating chamber, and first and second resistances; said constant current source being connected to one terminal of said thermistor and being connected to a plane of reference potential through said first resistance; said output terminal being coupled to said other terminal of said thermistor and being connected to said plane of reference potential through said second resistance, the sum of said first and second resistances being selected to substantially linearize the temperature-voltage characteristic of said analog output signal at said output terminal over a predetermined temperature range, the ratio of said resistances being selected to provide a desired voltage level on said output terminal at a selected temperature within said operating range; and
temperature display means coupled to said output terminal and linearly responsive to said analog output signal for producing an output display indicative of the output temperature of the fluid.

2. Fluid warming apparatus as defined in claim 1 wherein said first and second resistances comprise a potentiometer, the arm of said potentiometer being connected to said plane of reference potential and being adjustable to obtain said desired voltage level on said output terminal at said selected temperature.

3. Fluid warming apparatus as defined in claim 1 wherein said fluid is blood, and said predetermined operating range extends from approximately 30° C. to 40° C.

4. Fluid warming apparatus as defined in claim 1 wherein the sum ($R_1 + R_2$) of said first and second resistances is given by $$R_1 + R_2 = \frac{V_2 R_{T2} - V_1 R_{T1}}{V_1 - V_2}$$

where said temperature range extends from a temperature T1 to a temperature T2, and $V_1$ equals the desired output voltage at T1, $V_2$ equals the desired output voltage at T2, $R_{T1}$ equals the resistance of said thermistor at T1, and $R_{T2}$ equals the resistance of said thermistor at T2.

5. In a fluid warming apparatus for heating a refrigerated fluid such as blood to a predetermined nominal temperature, and of the type including a housing defining a heating chamber for the fluid, means including at least one electric heater element operable from an applied electric current in thermal communication with the fluid in said heating chamber for heating the fluid as it passes through the chamber.

control circuit means responsive to the output temperature of the fluid for generating a heater control signal, and switch circuit means electrically connected between said heating element and a source of electrical current, and responsive to said heater control signal, for controlling the application of current to said heating element to maintain the fluid at said predetermined nominal temperature, a temperature monitoring system comprising, in combination:

temperature sensing means for generating an analog output signal indicative of the output temperature of said fluid, said temperature sensing means including an output terminal, a constant-current source, a thermistor in thermal communication with said fluid at the output of said heating chamber, and first and second resistances; said constant current source being coupled to one terminal of said thermistor and being connected to a plane of reference potential through said first resistance; said output terminal being coupled to said other terminal of said thermistor and being connected to said plane of reference potential through said second resistance, the sum of said first and second resistances being selected to substantially linearize the temperature-voltage characteristic of said analog output signal at said output terminal over a predetermined temperature range, the ratio of said resistances being selected to provide a desired voltage level on said output terminal at a selected temperature within said operating range; and alarm generator means responsive to said output signal for generating an alarm upon the output temperature of said fluid exceeding said predetermined operating range.

6. A temperature monitoring system as defined in claim 5 wherein said first and second resistances comprise a potentiometer, the arm of said potentiometer being connected to said plane of reference potential and being adjustable to obtain said desired voltage level on said output terminal at said selected temperature.

7. A temperature monitoring system as defined in claim 5 wherein said fluid is blood, and said predetermined operating range extends from approximately 30° C. to 40° C.

8. A temperature monitoring system as defined in claim 5 wherein the sum ($R_1 + R_2$) of said first and second resistances is given by $$R_1 + R_2 = \frac{V_2 R_{T2} - V_1 R_{T1}}{V_1 - V_2}$$

where said temperature range extends from a temperature T1 to a temperature T2, and $V_1$ equals the desired output voltage at T1, $V_2$ equals the desired output voltage at T2, $R_{T1}$ equals the resistance of said thermistor at T1, and $R_{T2}$ equals the resistance of said thermistor at T2.

* * * * *